US00PP16120P2

(12) United States Plant Patent
Hammond

(10) Patent No.: US PP16,120 P2
(45) Date of Patent: Nov. 15, 2005

(54) ***GAURA* PLANT NAMED 'PERKY PINK'**

(50) Latin Name: *Gaura lindheimeri*
Varietal Denomination: Perky Pink

(75) Inventor: Frank Hammond, Nare Warren East (AU)

(73) Assignee: Evelyn Weidner, Encinitas, CA (US)

( * ) Notice: Subject to any disclaimer, the term of this patent is extended or adjusted under 35 U.S.C. 154(b) by 20 days.

(21) Appl. No.: 10/827,549

(22) Filed: Apr. 19, 2004

(51) Int. Cl.[7] ..... A01H 5/00
(52) U.S. Cl. ..... Plt./226
(58) Field of Search ..... Plt./226

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Gaura* plant named 'Perky Pink', characterized by its compact and outwardly spreading plant habit; freely branching growth habit; freely flowering habit; and light pink-colored flowers.

1 Drawing Sheet

Botanical classification/cultivar designation: *Gaura lindheimeri* cultivar Perky Pink.

BACKGROUND OF THE INVENTION

The present Invention relates to a new and distinct cultivar of *Gaura* plant, botanically known as *Gaura lindheimeri*, and hereinafter referred to by the cultivar name Perky Pink.

The new *Gaura* is a product of a planned breeding program conducted by the Inventor in Narre Warren East, Victoria, Australia. The objective of the breeding program is to create new compact *Gauras* with numerous flowers and attractive flower coloration.

The new *Gaura* originated from a open-pollination made by the Inventor in 1999 of the *Gaura lindheimeri* cultivar Siskiyou Pink, not patented, as the female, or seed, parent with an unknown selection of *Gaura lindheimeri*, not patented, as the male, or pollen, parent. The new *Gaura* was selected as a single plant from the resulting progeny of the open-pollination by the Inventor in 2000 in a controlled environment in Narre Warren East, Victoria, Australia.

Asexual reproduction of the new cultivar by terminal cuttings in a controlled environment in Narre Warren East, Victoria, Australia since October, 2000, has shown that the unique features of this new *Gaura* are stable and reproduced true to type in successive generations.

SUMMARY OF THE INVENTION

Plants of the cultivar Perky Pink have not been observed under all possible environmental conditions. The phenotype may vary somewhat with variations in environment such as temperature and light intensity without, however, any variance in genotype.

The following traits have been repeatedly observed and are determined to be the unique characteristics of 'Perky Pink'. These characteristics in combination distinguish 'Perky Pink' as a new and distinct cultivar of *Gaura:*

1. Compact and outwardly spreading plant habit.
2. Freely branching growth habit.
3. Freely flowering habit.
4. Light pink-colored flowers.

Plants of the new *Gaura* can be compared to plants of the female parent, the cultivar Siskiyou Pink. In side-by-side comparisons conducted in Narre Warren East, Victoria, Australia, plants of the new *Gaura* differed from plants of the cultivar Siskiyou Pink in the following characteristics:

1. Plants of the new *Gaura* were more compact and bushier than plants of the cultivar Siskiyou Pink.
2. Plants of the new *Gaura* had darker colored foliage than plants of the cultivar Siskiyou Pink.
3. Plants of the new *Gaura* and the cultivar Siskiyou Pink differed in flower color as plants of the cultivar Siskiyou Pink had red and white-colored flowers.

Plants of the new *Gaura* can also be compared to plants of other nonpatented selections of *Gaura lindheimeri* known to the Inventor. In side-by-side comparisons conducted in Narre Warren East, Victoria, Australia, plants of the new *Gaura* differed from plants of other known selections of *Gaura lindheimeri* known to the Inventor in the following characteristics:

1. Plants of the new *Gaura* were more compact and bushier than plants of other known selections of *Gaura lindheimeri* known to the Inventor.
2. Plants of the new *Gaura* had darker colored foliage than plants of other known selections of *Gaura lindheimeri* known to the Inventor.
3. Plants of the new *Gaura* and other known selections of *Gaura lindheimeri* known to the Inventor differed in flower color as plants of other known selections of *Gaura lindheimeri* known to the Inventor had white-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Gaura.*

The photograph at the top of the sheet comprises a side perspective view of a typical flowering plant of 'Perky Pink' grown in a container.

The photograph at the bottom of the sheet comprises a close-up view of typical flowers of 'Perky Pink'.

DETAILED BOTANICAL DESCRIPTION

The aforementioned photographs and following observations and measurements describe plants grown in Bonsall, Calif., under full sun conditions in an outdoor nursery during the spring and summer with day temperatures ranging from 18 to 35° C. and night temperatures ranging from 10 to 18° C. Three plants were grown in a 15-cm container and had been growing for about six weeks when the photographs and description were taken.

Color references are made to The Royal Horticultural Society Colour Chart, 1995 Edition, except where general terms of ordinary dictionary significance are used.

Botanical classification: *Gaura lindheimeri* cultivar Perky Pink.

Parentage:

*Female parent.*—*Gaura lindheimeri* cultivar Siskiyou Pink, not patented.

*Male parent.*—Unknown selection of *Gaura lindheimeri*, not patented.

Propagation:

*Type cutting.*—Vegetative cuttings.

*Time to initiate roots.*—About one to three weeks.

*Time to produce a rooted young plant.*—About four to five weeks.

*Root description.*—Fine, fibrous; white in color.

Plant description:

*Form.*—Compact and outwardly spreading plant habit. Freely branching growth habit with about seven or eight lateral branches per plant. Moderately vigorous growth habit.

*Plant height, soil level to top of foliar plane.*—About 10 to 12 cm.

*Plant height, soil level to top of inflorescences.*—About 56 cm.

*Plant diameter, single plant.*—About 12 cm.

*Lateral branches.*—Length: About 11 cm. Diameter: About 2.5 mm. Internode length: About 1.2 to 1.5 cm. Strength: Strong. Texture: Fine pubescence. Color: 144A.

*Foliage description.*—Arrangement: Alternate; simple. Length: About 6 cm. Width: About 1.3 cm. Shape: Linear to narrowly elliptic. Apex: Acuminate. Base: Attenuate. Margin: Entire. Texture, upper and lower surfaces: Slightly rough, grainy; glandular; upper surface, glabrous; lower surface, slightly pubescent. Venation pattern: Pinnate; arcuate. Color: Developing and fully expanded foliage, upper surface: 147A. Developing and fully expanded foliage, lower surface: 147B. Venation, upper and lower surfaces: 147B. Petiole length: About 4 mm. Petiole diameter: About 2 mm. Petiole texture, upper and lower surfaces: Smooth, glabrous. Petiole color, upper and lower surfaces: 144A.

Flower description:

*Flower type and habit.*—Solitary slightly zygomorphic flowers arranged on elongated terminal and axillary panicles. Flowers not persistent. Flowers face mostly outwardly about 45° from vertical. Flowers sessile.

*Quantity.*—Freely flowering; terminal panicles with typically about 30 to 40 flower buds and open flowers per inflorescence.

*Natural flowering season.*—Long flowering period; plants typically flower from April though October in Southern California; flowering continuous during this period.

*Flower longevity on the plant.*—About five to ten days.

*Fragrance.*—Not detected.

*Flower size.*—Length: About 2.5 cm. Width: About 2.5 cm. Depth: About 3 cm.

*Flower buds* (*showing color*).—Length: About 2 cm. Diameter: About 2 mm. Shape: Slender, elongated. Color: Towards the base, 59B; towards the apex, 146B.

*Petals.*—Quantity/arrangement: Four petals in a single whorl. Length: About 1.5 cm. Width: About 7 mm. Shape: Elongated oblong; cupped; claw-like. Apex: Broadly acute. Base: Attenuate. Margin: Entire. Texture, upper and lower surfaces: Smooth, satiny. Color: When opening, upper surface: 65D. When opening, lower surface: Lighter than 65D; towards the base, 65C. Fully opened, upper and lower surfaces: Lighter than 65D; venation, 65B.

*Sepals.*—Arrangement/appearance: Single whorl of four sepals. Length: About 1.8 cm. Width: About 2 mm. Shape: Linear.; reflexed. Apex: Acute. Base: Truncate. Margin: Entire. Texture, upper and lower surfaces: Smooth, glabrous. Color, immature: Upper surface: 64C. Lower surface: 186B. Color, mature, upper and lower surfaces: 186B.

*Peduncles.*—Length: About 10 cm. Width: About 1.5 mm. Angle: Upright to outwardly spreading; axillary peduncles, about 45° from vertical. Strength: Moderately strong. Texture: Smooth, glabrous. Color: 144A.

*Reproductive organs.*—Stamens: Quantity per flower: Eight. Anther shape: Linear. Anther size: About 1 mm by 4 mm. Anther color: 59A. Pollen amount: Scarce. Pollen color: 145C. Pistils: Quantity per flower: One. Pistil length: About 3.5 cm. Style length: About 1.8 mm. Style color: 155D; towards the apex, 62B. Stigma shape: Knobbed. Stigma color: 144C. Ovary color: 144A overlain with 59A.

*Fruit/seed.*—Fruit and seed production has not been observed.

Disease/pest resistance: Plants of the new *Gaura* have not been noted to be resistant to pathogens or pests common to *Gaura*.

Temperature tolerance: Plants of the new *Gaura* have been observed to tolerate temperatures from −4 to 38° C.

It is claimed:

1. A new and distinct cultivar of *Gaura* plant named 'Perky Pink', as illustrated and described.

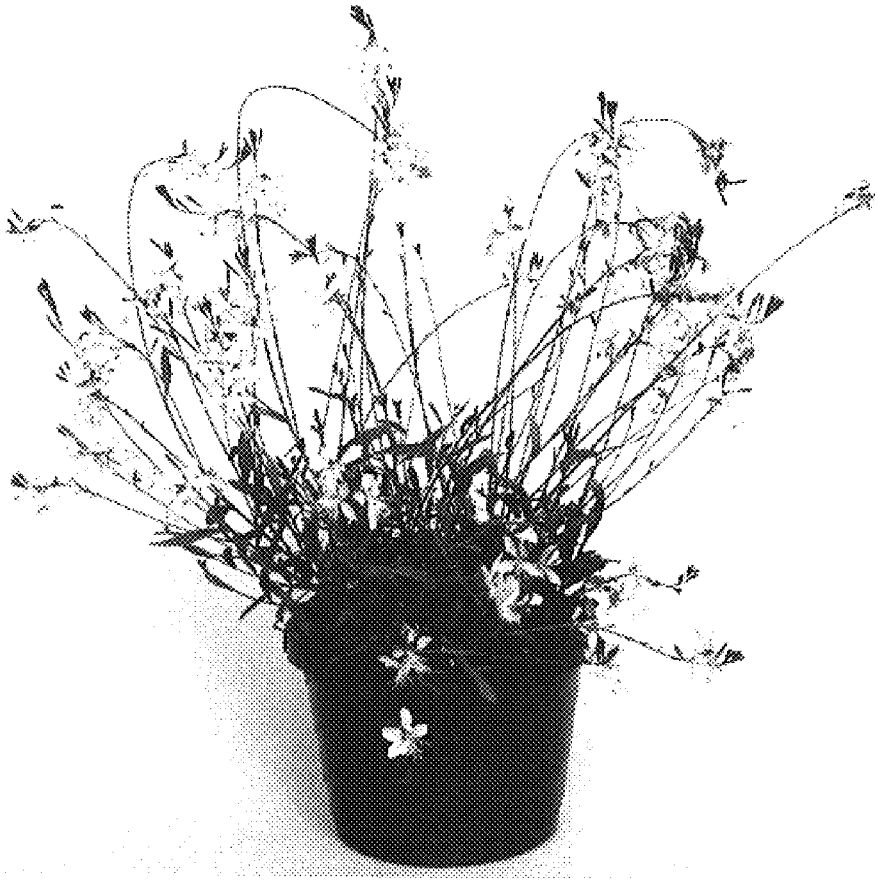
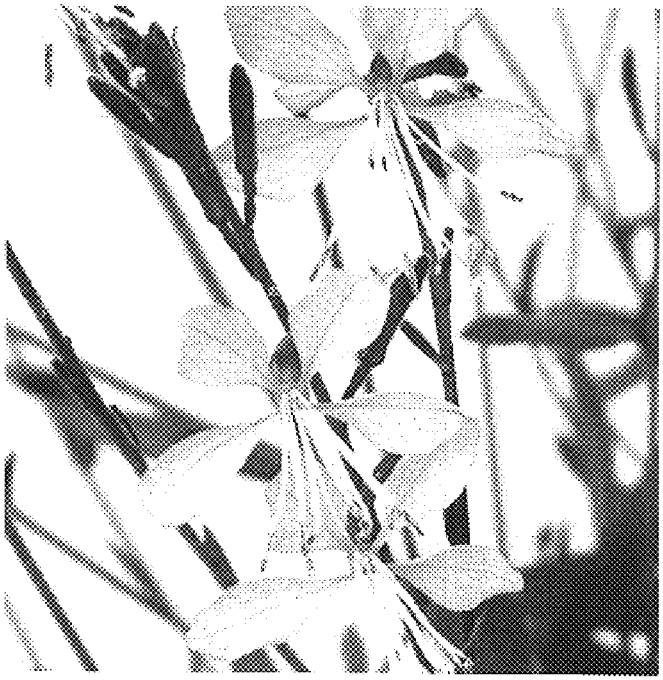

* * * * *